United States Patent [19]

Gawol et al.

[11] Patent Number: 4,702,116
[45] Date of Patent: Oct. 27, 1987

[54] PERMANENTLY NON-DUSTING PIGMENT AND DYE PREPARATIONS, METHOD FOR PRODUCING THEM, AND MEASURING DEVICE THEREFOR

[75] Inventors: Manfred Gawol, Clausthal-Zellerfeld; Gerhard Adrian, Goslar, both of Fed. Rep. of Germany

[73] Assignee: Dr. Hans Heubach GmbH & Co. KG, Langelsheim, Fed. Rep. of Germany

[21] Appl. No.: 873,367

[22] Filed: Jun. 12, 1986

Related U.S. Application Data

[63] Continuation-in-part of Ser. No. 763,437, Aug. 1, 1985.

[30] Foreign Application Priority Data

| Dec. 2, 1983 | [DE] | Fed. Rep. of Germany | 3343743 |
| Dec. 2, 1983 | [DE] | Fed. Rep. of Germany | 3343742 |
| Dec. 8, 1983 | [DE] | Fed. Rep. of Germany | 3344464 |
| Dec. 8, 1983 | [DE] | Fed. Rep. of Germany | 3344463 |

[51] Int. Cl.⁴ .................. G01N 5/00; G01N 19/00; G01N 33/00; G01N 33/22
[52] U.S. Cl. .................. 73/865.6; 73/150 R; 73/866; 8/400
[58] Field of Search .................. 73/866, 865.6, 866.4, 73/865.5, 38, 61 R, 150 R; 8/400

[56] References Cited

U.S. PATENT DOCUMENTS

| 3,499,315 | 3/1970 | Marino | 73/38 X |
| 3,636,772 | 1/1972 | Bennett | 73/866 |
| 3,778,287 | 12/1973 | Stansfield et al. | 106/308 Q |
| 4,069,013 | 1/1978 | Hett et al. | 8/79 |
| 4,079,621 | 3/1978 | Batzer | 73/866 X |
| 4,117,717 | 10/1978 | Isley | 73/38 |
| 4,143,539 | 3/1979 | Baillie | 73/866 X |
| 4,295,851 | 10/1981 | Neumann et al. | 8/524 |
| 4,402,702 | 9/1983 | Kaspar et al. | 8/524 |
| 4,425,134 | 1/1984 | Bruttel et al. | 8/524 |

FOREIGN PATENT DOCUMENTS

| 0023638 | 2/1981 | European Pat. Off. . |
| 0026489 | 4/1981 | European Pat. Off. . |
| 0056160 | 7/1982 | European Pat. Off. . |
| 274642 | 2/1913 | Fed. Rep. of Germany . |
| 2523096 | 11/1976 | Fed. Rep. of Germany . |
| 2723921 | 12/1977 | Fed. Rep. of Germany . |
| 2841566 | 4/1980 | Fed. Rep. of Germany . |
| 2931771 | 2/1981 | Fed. Rep. of Germany . |
| 1061307 | 4/1954 | France . |
| 2119583 | 8/1972 | France . |
| 2373593 | 7/1978 | France . |
| 147040 | 11/1981 | Japan | 73/865.6 |
| 576100 | 3/1946 | United Kingdom . |
| 1442538 | 7/1976 | United Kingdom . |
| 1442583 | 7/1976 | United Kingdom . |
| 1558183 | 12/1979 | United Kingdom | 73/865.6 |
| 894183 | 12/1981 | U.S.S.R. | 73/865.6 |

OTHER PUBLICATIONS

"Colloids"; *Kirk-Othmer Encylopedia of Chemical Technology 3rd Ed. Supplement Volume Alcohol Fuels to Toxicology*; pp. 241-259; Alan Bleier; pub. by John Wiley & Sons, Inc., 1984.

Chem. Abstrct, vol. 96, No. 22, (1982), 182693r, "Non-dusting and rapidly wettable vat dyes with medium and high dispersibility". (p. 84)

*Primary Examiner*—Tom Noland
*Attorney, Agent, or Firm*—Browdy and Neimark

[57] ABSTRACT

The dust producing properties of a pigment or dye are measured under conditions which close approximate those during handling. A vessel with baffles having pigment or dye therein is rotated for a specified time while air is drawn through the rotating vessel by a specified amount of vacuum applied downstream of the vessel. The baffles disturb the pigment or dye in the vessel, creating dust particles which are entrained in an airstream created by the vacuum. Larger particles trapped in this vacuum are removed by a separator, while the dust particles are trapped in the airstream are trapped by a filter. The dusting properties of the pigment or dye in the vessel may then be determined by weighing the filter.

9 Claims, 4 Drawing Figures

PERMANENTLY NON-DUSTING PIGMENT AND DYE PREPARATIONS, METHOD FOR PRODUCING THEM, AND MEASURING DEVICE THEREFOR

CROSS-REFERENCES TO RELATED APPLICATIONS

This is a continuation-in-part application of parent, copending application Ser. No. 763,437, filed Aug. 1, 1985, originally filed on November 30, 1984, as PCT/EP 84/00380

BACKGROUND OF THE INVENTION

1. Field of the Invention

The present invention relates generally to devices for measuring the dusting properties of a substance, and more particularly to devices for measuring the dusting properties of pigments and dyes.

2. Description of the Related Art

In the field of pigments and dyes, there are increasing attempts being made to produce dust-free and non-dusting preparations, which do not emit dust while being processed. Such non-dusting preparations are particularly desirable so as to avoid color contamination when various products are handled, and they also make accurate apportioning possible. Dust losses are avoided, and because it is cleaner and safer to work with such preparations, the health risk involved in working with toxic pigments and dyes is also reduced.

The safest procedure is to use paste preparations, adding enough of such additives as surface-active substances and solvents as to attain a non-dusting, pasty state. The agents required for a particular application, such as dispersing agents, anti-settling agents and binders, are often also incorporated at the same time. In such pastes, the pigment concentration depends on the fineness and texture of the given pigment as well as on the amount of binder it requires and may be between approximately 30 and 90%. In producing the pigment pastes, the starting material is dried pigment, which is mixed with the various components.

The disadvantage of the pigment pastes is that they are difficult to apportion, and they necessitate careful cleaning of the packing drum.

Quite a number of methods are already known. According to German patent application DE-OS No. 27 23 921, the tendency of metal chromates to produce dust is suppressed by adding a combination of phthalic and terephthalic acid esters and esters of fatty acids, along with surface-active substances, to an aqueous suspension of pigment and drying it after filtration. Such preparations produce less dust, but they are not permanently non-dusting. A product produced according to Example 1 of the above patent application yielded a dust production value of 83 mg/100 g, as measured with the Heubach dust-production measuring device. Further methods and agents are disclosed in German patent application DE-OS No. 29 31 771 and DE-OS No. 25 23 096, U.S. Pat. No. 3,560,134, European patent application EU-OS No. 0056 160 and German patent application DE-OS No. 28 41 566.

The parent application, U.S. patent application Ser. No. 763,437, filed Aug. 1, 1985, discloses and claims permanently non-dusting pigment and dye preparations, which in addition to from 75 to 97.5% pigment contain a surface-active substance in an amount from 0.5 to 10% and from 2 to 25% of an agent which when intensive shear stress is applied causes the dried, homogeneous mixture of pigment or dye and surface-active substance to reach the smear point, which preparations are at the smear point as defined herein. Any surface-active agent suitable for the particular pigment or dye type used and for the intended later application can be used as the surface-active substance; exeamples include ionic or nonionic agents available on the market. However, a long-chain polyester of the "highly effective dispersing agent" type is particularly preferred, in particular a polyester derived from a saturated or unsaturated aliphatic $\omega$-hydroxycarboxylic acid with at least 4 carbon atoms between the hydroxy group and the carboxy group and a total of at least 9 carbon atoms including the carboxy group, or from a mixture of a hydroxycarboxylic acid of this kind and a carboxylic acid lacking hydroxy groups, in particular one having up to 20 carbon atoms.

Among these suitable polyesters are those described in German patent application DE-OS No. 21 62 484, which are hereby expressly incorporated by reference.

What is essential here is that the surface-active substance is not applied to the dry pigment, nor has the pigment already been dried; instead, the still-moist pigment, as it comes from the production process, is treated with the surface-active substance, because otherwise the desired surface properties are not obtained. Therefore the agent is suitably also mixed with the pigment suspension and only then is it dried. The term "pigment" also includes dyes.

Any substance that, after being introduced into the dry mixture of pigment and surface-active substance that is to be attained, causes the mixture to attain the smear point under intensive shear stress can be used, and the various technical requirements of the fields of application, such as enamels, paints, printing inks and plastic dyes, can be taken into consideration at the same time. Among these are water, organic solvents, plasticizers and substances which become liquid in response to elevated temperatures, such as waxes. Useful agents here are those which either do not volatilize, or do not do so significantly. For reasons of economy, mineral oil is generally preferred, because it brings about excellent results and is relatively inexpensive.

As the mineral oil, aliphatic, alicyclic and/or aromatic hydrocarbons which are flowable at room temperature and the boiling point of which is above 70° C. are particularly useful. Aliphatic hydrocarbons which may contain various quantities of cycloaliphatic and/or aromatic hydrocarbons are preferred. This category thus includes not only technical grade mineral oils made from variously refined crude oils but also synthetic hydrocarbons, such as Fischer-Tropsch mixtures with the given boiling ranges. Accordingly, this includes all unsaponifiable substances of arbitrary origin, mainly comprising hydrocarbons, obtained for example from crude oil, froms tars or the distillation products thereof, or from low-temperature carbonization.

Special preference is given to synthetic isoparaffins. However, water is also very suitable, and in particular from 10 to 15% of water can be added when small quantities of surface-active agent are employed. In the case of preparations made non-dusting by the addition of water, the end product should then be packaged in watertight or vapor-tight containers, so that no significant amounts of water can escape.

These permanently non-dusting pigment preparations are produced by adding 0.5 to 10% by weight, relative to the total weight of the end product, of a suitable surface-active agent to the filter suspension of the pigment; after homogeneous distribution, the combination of pigment and surface-active agent, which may optionally have been isolated in the form of a press cake, is dried, and the dried product is then mixed with an agent which brings the mixture to the smear point when intensive shear stresses are applied, this agent being in particular mineral oil having a boiling range from 70° to 360° C., preferably 180° to 280° C., and especially 180° to 250° C.; intensive shear stress is applied until the smear point is reached, and then the product is granulated in a manner known per se if desired.

If water is to be used as the substance that brings the mixture to the smear point, this water can be added subsequently, or else the mixture of pigment or dye and surface-active agent, the latter perhaps in the form of a press cake, is not fully dried, so that a residual water content of 2 to 25%, and in particular 10 to 15%, remains, and the moist mixture thus obtained is brought to the smear point by the application of shear stress and, if desired, granulated. This water content is then present in the end product as well, aside from slight changes occurring during further processing.

The homogeneous distribution of the surface-active substance in the filter suspension of the pigment is achieved by performing thorough mixing in a known manner. Isolation as a press cake is achieved by means of suitable filtration devices, such as filter presses, drum filters, suction filters, etc., which yield a press cake or an equivalent adequately water-free product which can then be dried in a technically appropriate manner.

Treatment with the substance which brings the mixture to the smear point is carried out in such mixing apparatus as a kneader mixer, intensive mixer, paddle mixer or any other suitable device which generates sufficient shear stress and brings the product to the smear point within no longer than approximately 2 hours. Preference is given to degrees of shear stress by which the smear point is attained within 15 to 45 minutes, and in particular within about half an hour. In the process, the product usually appears in the form of a flowable fine granules which is practically non-dusting.

Within the meaning employed in this patent application, the smear point is reached when a cohesive, putty-like mass, as defined for example by determining the oil adsorption according to DIN 53199 (see also Ullmanns Encyklopaedie der technischen Chemie [Ullman's Encyclopedia of Industrial Chemistry], 4th edition, Volume 18, page 565), has not yet formed. The smear point as defined in this patent application is reached when the above-mentioned flowable fine granulate, which is non-dusting, has formed and produces a slight smearing effect on the walls of the mixing devices. Hence the amount of dust-binding agent, such as oil, required to achieve this smear point is less than the amount of oil required to determine the oil adsorption according to DIN 53199 and is shown in Henry A. Gardner and George C. Sward, "Paints, Varnishes, Lacquers and Colors", 12th Edition, March, 1962, distributed By Gardner Laboratory, Inc., as Stage A and 2 bottom pictures on page 245, FIG. 443 and is about or shortly before the "wet point" as shown on pages 251-253.

By adding the surface-active substance to the pigment suspension before drying is carried out, optimum wetting is achieved, which makes it possible to obtain a virtually absolutely non-dusting pigment preparation by adding mineral oil, for example, to the dried product comprising pigment and surface-active substance. Only relatively small quantities of mineral oil are needed. When equal amounts of surface-active substance and mineral oil are added to the previously dried product, almost twice as much mineral oil is needed, e.g., more than 20%, instead of 10% as in the method according to the present invention, to achieve the same degree of absence of dust production.

This method can be applied in principle to all pigments and dyes which are in the wet state and are separated out as a filter suspension. It can be used equally well for inorganic and organic pigments and dyes such as lead chromate, lead molybdate, zinc chromate, mixed-phase pigments such as nickel-titanium yellow, chrome-titanium yellow, etc., phthalocyanines, anthraquinones, azo pigments, lake-type azo pigments, disazo condensation pigments, isoindolines, indigold dyes, quinachridones, and perylenes, among others.

The mixture of pigment or dye suspension, which usually contains about 50% water, and surface-active agent is first thoroughly homogenized and then either dried directly or, if it is desired that the water content be reduced further, it is further dewatered in a suitable press, for instance a high-pressure press, and only then taken to the drying stage, thereby saving drying costs. In this way it is possible to obtain press cakes having a solids content of up to 85%. This mixture can be dried in the usual manner, for instance on belt or suspended-belt dryers with an ambient temperature of 120° to 130° C., or in vacuum dryers where temperatures of 100° to 120° C. are normally used. Since the mixture contains organic material, care should be taken to insure that the drying conditions, in particular the temperature, do not cause any damage to the material, for instance by local overheating.

The present dust production measuring device was developed in order to be able to perform extremely accurate analyses of the dust-producing tendencies of powdered and granular substances, because quantitative information about dust-producing behavior is important for the sake of safe industrial processes and operations. The tendency toward dust production was heretofore judged by analogy with the proportion of fines in the starting material, or by estimation, but such methods can give rise to considerable errors, because dust particles are frequently generated only by some type of movement and by abrasion; in contrast, the tendency to produce dust during materials handling is ascertained herein in a manner that very closely approximates actual conditions. To this end, the test material remains in motion during the entire period of measurement.

SUMMARY OF THE INVENTION

It is an object of the present invention to overcome the above-stated disadvantages of prior art devices for measuring dust production.

It is another object of the present invention to provide a device for measuring dust production in a pigment or dye under conditions which approximates actual handling conditions of the pigment or dye.

These objects and others are achieved by the present invention. A rotating vessel, with baffles, has a pigment or dye placed therein. The baffles disturb the pigment or dye, while a vacuum draws air through the rotating vessel. Downstream of the rotating vessel, a separation means removes larger pigment or dye particles carried by the airstream formed by the vacuum. Downstream of the separation means, a filter traps entrained dust particles. The dusting properties of the pigment or dye in the vessel may be determined by weighing the filter after the container has been rotated under a specified amount of vacuum for a specified time.

BRIEF DESCRIPTION OF THE DRAWINGS

Exemplary embodiments of the invention are elucidated below by way of the drawing. There is shown in.

DESCRIPTION OF THE PREFERRED EMBODIMENTS

Figure 2:
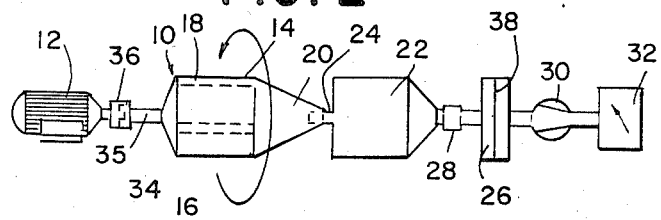
FIG. 2 a detailed embodiment of a dust production measuring device, which is suited particularly for gravimetric evaluations and chemical analysis.
Figure 1:
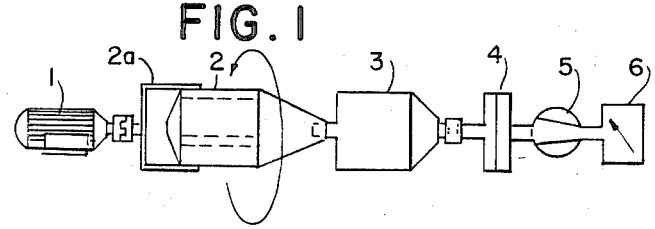
FIG. 1 a diagrammatic representation of the dust production measuring device.
Figure 3:
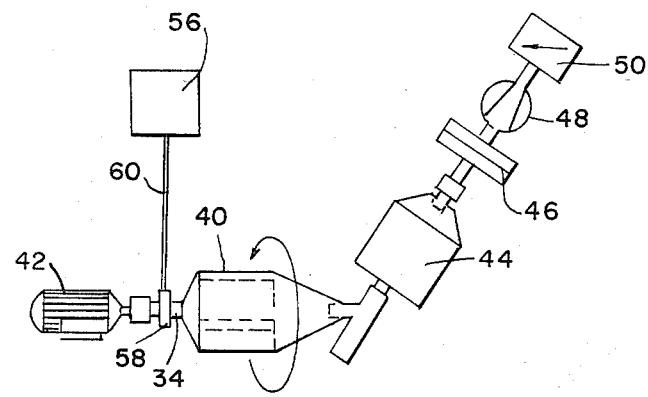
FIG. 3 a detailed embodiment of a dust production measuring device, which is suited for the detection of traces; and in FIG. 4 an interior view of a dust generating vessel.
Figure 4:
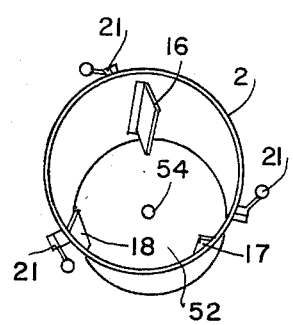

FIG. 1 shows that the powder or granular material is kept in motion in a dust-generating vessel 2, having a 2.5 liter capacity for 5 minutes at 30 rpm. Built-in baffles simulate events during conveyance, and the dust particles are picked up by an air flow which carries them out of the dust-generating vessel and deposits them on a filter 4 having a defined porosity. Coarser particles are retained in a coarse separator 3. The air is drawn through the system by a vacuum pump 5, and it is also recorded by an air lock equipped with an air flow meter 6 and discharged. A motor 1 drives the system. The holder 2a may hold the vessel 2, or the vessel may be directly connected by a shaft with the motor. FIGS. 2 to 4 show detailed embodiments.

The dust production measuring device depicted in FIG. 2 consists of a dust-generating vessel 10 which is rotatably driven through a motor 12. The dust-generating vessel 10 includes a cylindrical container 14, with baffle plates 16, 18 being built thereinto. The cylindrical container 14 is closed by means of a conically designed cover (lid) member 20. The connection of parts 14 and 20 takes place through suitable means, such as, for example screw-connection or toggles (clamp handles).

Subsequent to the dust-generating vessel 10 there is arranged a vessel 22, which is provided for separating coarse dust particles. The dust-generating vessel 10 and the coarse separator 22 are connected to one another through a short piece of pipe 24.

A filter 26 is connected behind the coarse separator 22. The connection between the coarse separator 22 and the filter 26 takes place through a pipe section 28. Behind filter 26 there is arranged a vacuum pressure pump 30, which is controlled via a measuring and regulating module 32. The flow rate and the air quantity can be pre-selected and precisely controlled via the measuring and regulating module 32.

In operation, the material to be tested is introduced into the dust-generating vessel, which may for that purpose be opened. The dust-generating vessel of FIGS. 2 and 3 is provided with a hollow shaft 34, which is connected via a coupling 36 with the motor 12. The hollow shaft is designed to have four apertures 35 distributed over the circumference. After closing and positioning of the dust-generating vessel 10, motor 12 is switched on, thus causing vessel 10 to rotate. At the same time, pump 30 is switched on through the measuring and regulating module 32, so that there is generated by said pump an axially directed air stream through the apertures 35 in the hollow shaft 34, through the vessel 10 via the pipe section 24, the coarse separator 22, the pipe section 28 and the filter 26. Entry of air may, however, also take place through holes in the bottom of vessel 2, e.g. in a case where vessel 2 is connected through retainer 2a to the motor. The baffle plates 16, 18 built into the vessel 10 simulate conveyance events such as they are encountered in practice. The dust generated in vessel 10 is taken up by the air stream entering axially into the vessel through the hollow shaft, and it is, after particles that cannot fly have been separated in the coarse separator 22, deposited on a filter 38 of defined (specific) porosity that is arranged in the filter housing 26. The dust-generating vessel 10 likewise has a capacity of e.g. 2.5 l. Depending upon density, there are introduced up to 100 g of the test substance, and the dust-generating vessel 10 is driven for 5 minutes at 30 rpm. The throughflow of air produced via pump 30 is e.g. 0.25 l/sec. After completion of the test run, the filter 38 is removed and the proportion of dust determined by means of weighing.

The embodiment shown in FIG. 2 is suited, in particular, for gravimetric evaluation and chemical analysis. FIG. 3 depicts a dust production measuring device, which is suited particularly for the detection of traces, i.a. through high pressure liquid chromatography. This device consists of a dust-generating vessel 40, which is driven through a motor 42. A coarse separator 44 arranged subsequent to the dust-generating vessel and a filter 46 having defined (specific) porosity are not oriented coaxially to the dust-generating vessel but, rather, at an appropriate angle to the axis of the dust-generating vessel. In that way, a greater dust proportion is retained in the coarse separator 44 than in the case of the embodiment according to FIG. 2. Dust particles of very minor magnitude (size) only are then collected in filter 46. An air stream directed out of the dust-generating vessel 40 and through the coarse separator 44 and through the filter 46 is created via a pump 48, which is controlled through a measuring and regulating module 50. Operation of the devices according to FIGS. 2 and 3 occurs in the same way as that of the device according to FIG. 1, the operating values being variable depending upon the test sample.

FIG. 4 shows a view into the interior of the cylindrical dust-generating vessel 2. Baffle plates 16, 17, 18 are built into the interior of the vessel 2, which plates are designed in the form of vanes or blades and are attached to the inside wall. The connection to the conical closure member 20 takes place through toggles 21. An aperture 54 is formed in the central region of the bottom 52 of vessel 14, through which aperture air can be aspirated to the interior of the vessel when pump 30 is in operation. The aperture is in communication with the hollow shaft 34, so that air can flow through apertures in the hollow shaft 34 through the aperture 54.

In the embodiment depicted in FIG. 3, a cuff 58 sealed via O-rings is arranged on the hollow shaft 34 in the region of the apertures. Cuff 58 is in communication via a conduit 60 with a means for introducing a gas into vessels, such as drying tower 56, from which dried air is aspirated into vessel 40. In a case where it is intended to examine the dust-generating behavior of hygroscopic materials, a suitable gas is taken via conduit 60 from a source of that gas, so that the dust-generating behavior can be simulated with said gas.

Compared with a dust production measuring device, in which the dust value is measured by the attenuation of a beam of light passing through a collecting container, the attenuation being caused by the swirling up of dust produced when the test sample is dropped once into the container, the device according to the invention has the advantage that it measures a state that very closely approximates that encountered in actual practice, such as during conveying, mixing and filling operations.

| Test Data: | |
| --- | --- |
| Sample weight | 100 g |
| Measuring time | 5 min |
| Speed | 30 rpm |
| Air flow | 0.25 liters/sec |
| Dust-generating vessel | 2.5 liter capacity |

The following examples will explain the invention. A non-dusting preparation is assumed to be one which yields dust production values of 0 to a maximum of 5 mg/100 g when measured with the Heubach dust production measuring device.

EXAMPLE 1

1 kg of chromate pigment suspension was combined with 15 g of the polyester-based surface-active substance and well mixed with the aid of a stirrer. Following drying, the pigment was mixed with 10% of mineral oil in a kneader or paddle mixer and the intensive mixing was continued until such time as a uniform distribution of the additives was achieved. This state is recognized from the fact that a flowable, non-dusting fine granulate is formed. Usually this takes about 30 minutes. The treated finished product was measured using the Heubach dust production measuring device, and a dust production value of 0 mg/100 mg of pigment was obtained. The non-treated, dried pigment sample yielded a dust production value of 90 mg/100 g.

EXAMPLE 2

10 g of polyester-based surface-active substance was added to 1 kg of 50% zinc chromate suspension and mixed by stirring well. Following drying, the pigment was mixed with 13% of mineral oil in a kneader or paddle mixer and then subjected to the shear effects of the mixing device until the mineral oil was fully homogeneously distributed. After about 30 minutes, a non-dusting, flowable fine granulate was obtained having a dust production value of 0, as measured by the Heubach dust production measuring device. The untreated, dried sample of zinc chromate pigment yielded a dust production value of 250 mg/100 g.

EXAMPLE 3

300 g of phthalocyanine press cake (approximately 36% solids) was combined with a mixture of 150 g isopropanol, 5.5 g aminomethyl propanol and 8.2 g of the polyester-based surface-active substance; then, after the addition of 100 g of water, it was stirred for about 30 minutes with a dissolver. The pigment suspension prepared in this way was dried in a drying cabinet and after intermediate grinding in a laboratory mill it was mixed in a mixer with 20% of mineral oil (relative to the solids content) and the intensive mixing was continued until homogeneous distribution of the additives was achieved. After 20 to 30 minutes, a non-dusting, flowable fine granulate had formed, the dust production value of which was 5 mg/100 g when measured with the Heubach dust production measuring device. Non-prepared phthalocyanine pigments have dust production values of 2500 to 3500 mg/100 g.

EXAMPLE 4

A mixture of 23 g of aminomethyl propanol and 25 g of the polyester-based surface-active substance was added to 1568 g of an anthraquinone pigment suspension (solids content approximately 28%) and stirred for about 30 minutes in a dissolver. In order to prevent foaming, 7.5 g of a defoaming agent were also added. The suspension prepared in this way was dried in a drying cabinet and then pre-ground in a laboratory mill.

The preparation was placed in a mixer and combined with 20% of mineral oil, and then mixing was continued for about 30 minutes. This yielded a flowable, non-dusting fine granulate with a dust production value of less than 5 mg/100 g of pigment as measured with a Heubach dust production measuring device. Dried, unprepared anthraquinone pigments have extraordinarily high dust production values of 3500 to 4500 mg/100 g.

EXAMPLE 5

1 kg of 50% chromate pigment suspension was combined with 15 g of the polyester-based surface-active substance and well mixed with the aid of a stirrer. Following drying, the pigment was combined with 15% of molten wax in a heatable kneader mixer and intensive mixing was performed until uniform distribution of the additive had been achieved. This state is recognized from the fact that a flowable non-dusting granulate is formed. Generally, this takes about 30 minutes to occur. The pigment was first brought to a temperature that was above the melting point of the wax. A wax with a melting point of 79° C. was used.

The dust production measured for the preparation produced in this way was 5 mg/100 g. The measurement was performed with a Heubach dust production measuring device.

Naturally the auxiliary agents, such as dispersing or anti-abrasion agents, which are required for specific applications can be added directly to the preparation according to the invention. Such agents are suitably added together with the addition of the agent (b) which brings the mixture to the smear point. Similarly, as demonstrated in one of the examples, auxiliary agents for the mixing or kneading process, such as anti-foaming agents, can be added during the appropriate stage. All these auxiliary agents are used in the technically customary and well-known quantities, which can be determined by performing a few preliminary experiments for a particular case, i.e., as a function of the quantity and type of the surface-active agent and the quantity and type of the agent that brings the mixture to the smear point.

The following preferred embodiments of the invention are named:

As additive b, an additive which is liquid, or becomes liquid above 50° C., is present in the preparations. As the liquid additive, water, in particular, or a mineral oil with a boiling range up to 360° C., preferably 180°–280° C., can be present, while the additive that is liquid at the higher temperature preferably has a melting point of from 50° to 200° C. The substance leading to the smear point is added in a quantity of from 2 to 25% by weight, in terms of the end product, or (if evaporation takes place) in a quantity such that a content of 2 to 25% by weight is attained in the end product. In the case of mineral oil, the additive preferably amounts to 5 to 15%, in particular 10%. The additive that becomes liquid above 50° C. can in particular be a wax or paraffin substance. The filter suspension of the pigment or dye that is homogenized with the surface-active substance is isolated in the form of a press cake by means of suitable filter systems, such as a filter press, suction press, drum filter and the like.

It is essential that what is treated with the surface-active agent is the still-moist pigment, dewatered only mechanically, for instance being pressed out or centrifuged, but even if a slight drying effect occurs, for instance by air or warm air drying, still generally moist. That is, the surfaces of the pigment particles are not dried but are instead still moist, even if the dampness on these surfaces is reduced as compared with the moistness within the filter suspension press cake. The term "pigment" here encompasses dyes as well.

We claim:

1. A device for measuring the dust production behavior of a pigment or dye preparation at conditions approximating actual practice, comprising a dust-generating vessel (2), which is rotated about an axis thereof by a drive motor (1) and includes built-in baffles which simulate conveyance phenomena;

a pump (5) for generating an air flow for carrying dust particles discharged from the dust-generating vessel (2);

a filter (4) having a defined porosity positioned downstream of the dust-generating vessel;

a coarse separator (3) for retaining coarser particles disposed between the filter (4) and the dust-generating vessel (2); and an air lock, positioned downstream of said filter, having an air flow meter (6) which measures the air flow, where the air flow is discharged.

2. Device according to claim 1, wherein the air flow is fed axially into the dust generating vessel (2).

3. Device according to claim 1, wherein the pump is a vacuum pressure pump having opposing sides, and which, during operation, creates a vacuum at one side thereof and above atmospheric pressure at the opposite side thereof.

4. Device according to claim 1, wherein there is a measuring and regulating module (6,32) downstream of the pump.

5. Device according to claim 1, wherein the dust-generating vessel is connected with the motor by a hollow shaft, which hollow shaft contains openings for introducing air into the hollow shaft and the dust generating vessel.

6. Device according to claim 1, wherein the hollow shaft is connected by openings (35) with a tube connected to a means for introducing a gas into said dust generating vessel.

7. The device of claim 1, wherein all of said built-in baffles are attached to an inner peripheral wall of said vessel.

8. The device of claim 1, further comprising means for rotating said dust-generating about said axis vessel at about 30 rpm, said dust-generating vessel being essentially cylindrical and having a capacity of about 2.5 liters.

9. The device of claim 1, wherein said built-in baffles extend in an essentially axial direction.

* * * * *